(12) United States Patent
Heinzle et al.

(10) Patent No.: US 11,884,458 B2
(45) Date of Patent: Jan. 30, 2024

(54) LIQUID DISPENSER WITH SECURING MECHANISM

(71) Applicant: Aptar Radolfzell GmbH, Radolfzell (DE)

(72) Inventors: Volker Heinzle, Krauchenwies (DE); Julian Trinkner, Volkertshausen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 0 days.

(21) Appl. No.: 17/590,366

(22) Filed: Feb. 1, 2022

(65) Prior Publication Data

US 2022/0250811 A1 Aug. 11, 2022

(30) Foreign Application Priority Data

Feb. 9, 2021 (EP) ..................... 21155900

(51) Int. Cl.
*B65D 47/12* (2006.01)
*B65D 47/20* (2006.01)
(Continued)

(52) U.S. Cl.
CPC .......... *B65D 47/128* (2013.01); *A61F 9/0008* (2013.01); *A61J 1/00* (2013.01); *A61M 11/008* (2014.02); *B65D 23/00* (2013.01); *B65D 35/46* (2013.01); *B65D 41/32* (2013.01); *B65D 47/18* (2013.01); *B65D 47/2075* (2013.01); *B65D 50/00* (2013.01); *B65D 51/1611* (2013.01); *B65D 51/1616* (2013.01);
(Continued)

(58) Field of Classification Search
CPC ...... B65D 47/128; B65D 35/46; B65D 41/32; B65D 47/2075; B65D 51/1611; B65D 51/1616; B65D 51/1677; B65D 2205/02; B65D 47/18; B65D 23/00; B65D 50/00; A61M 15/0025; A61M 15/0081; A61M 2205/276; A61M 11/008; A61F 9/0008; A61J 1/00
See application file for complete search history.

(56) References Cited

U.S. PATENT DOCUMENTS 5,385,272 A * 1/1995 Aoun ................... A47K 5/1215
222/213
10,781,020 B2 * 9/2020 Greiner-Perth ...... B01D 61/147
(Continued)

FOREIGN PATENT DOCUMENTS

DE 102016210992 B3 5/2017
DE 202018103271 U1 8/2018

OTHER PUBLICATIONS

European Search Report issued in corresponding European Application No. 21 15 5900.0 with English translation of categories of cited documents, dated Jul. 26, 2021 (9 pages).

*Primary Examiner* — Frederick C Nicolas
(74) *Attorney, Agent, or Firm* — FLYNN THIEL, P.C.

(57) ABSTRACT

A liquid dispenser is for the delivery of pharmaceutical liquids, including a droplet dispenser, the liquid reservoir thereof being formed by a squeezable bottle body. Two measures secure the liquid dispenser, namely the provision of a cover body, an application of force on the squeezable bottle body being able to be prevented thereby, as well as a cap with a rotatable locking ring. The removal of the cap and the transfer of the cover body into a use position requires the deformation of an annular partial element.

28 Claims, 6 Drawing Sheets

(51) Int. Cl.
- *B65D 35/46* (2006.01)
- *B65D 41/32* (2006.01)
- *B65D 51/16* (2006.01)
- *B65D 23/00* (2006.01)
- *B65D 47/18* (2006.01)
- *A61F 9/00* (2006.01)
- *B65D 50/00* (2006.01)
- *A61M 11/00* (2006.01)
- *A61J 1/00* (2023.01)
- *A61M 15/00* (2006.01)

(52) U.S. Cl.
CPC ..... *B65D 51/1677* (2013.01); *A61M 15/0025* (2014.02); *A61M 15/0081* (2014.02); *A61M 2205/276* (2013.01); *B65D 2205/02* (2013.01)

(56) References Cited

U.S. PATENT DOCUMENTS

| | | | |
|---|---|---|---|
| 2014/0263456 A1* | 9/2014 | Barber | B65D 47/127 222/153.13 |
| 2017/0362000 A1 | 12/2017 | Greiner-Perth et al. | |

* cited by examiner

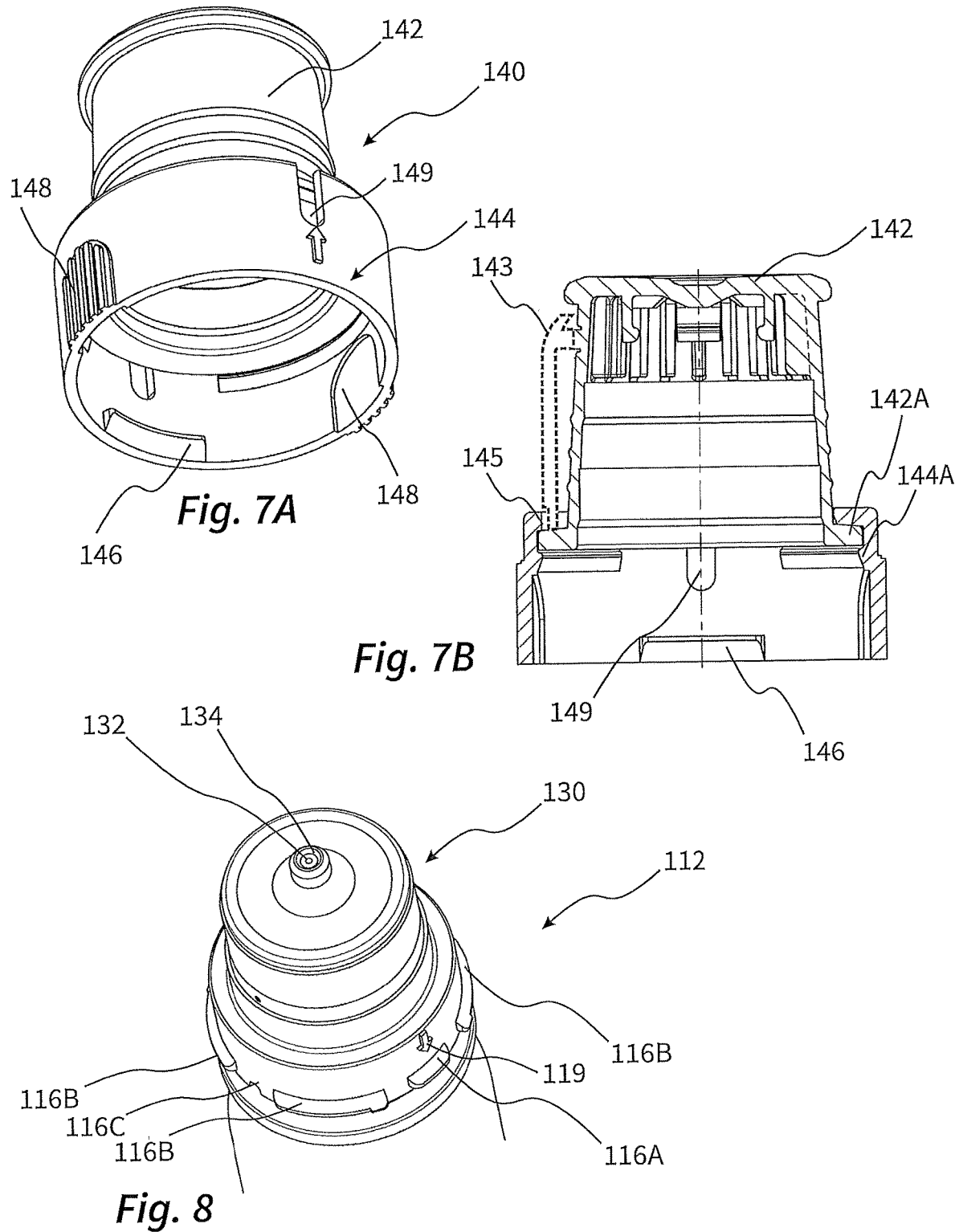

LIQUID DISPENSER WITH SECURING MECHANISM

CROSS-REFERENCE TO RELATED APPLICATION

This claims priority from European Application No. 21155900.0, filed Feb. 9, 2021, the disclosure of which is hereby incorporated by reference in its entirety.

FIELD OF APPLICATION AND PRIOR ART

The invention relates to a liquid dispenser for the discharge of pharmaceutical liquids. The invention relates, in particular, to liquid dispensers which are provided for the discharge of liquids in the form of individual droplets, for example for the application of eye drops into the eyes of the patient.

A generic liquid dispenser preferably has a squeezable bottle body which forms the liquid reservoir. The liquid contained therein may be delivered by applying force on either side. To this end, a delivery head which has a delivery opening is fastened to a container neck of the squeezable bottle body.

The liquid dispensers described herein generally contain pharmaceutical liquids, the ingestion thereof by children potentially being harmful to health. This is problematic, in particular in the case of squeezable bottle dispensers, since in this case a delivery may be brought about even by young children who randomly compress the squeezable bottle body and thereby bring about a delivery of liquid.

OBJECT AND SOLUTION

It is an object to develop a liquid dispenser such that the risk of an inadvertent delivery of liquid is reduced.

According to a first aspect of the invention, a liquid dispenser which has a squeezable bottle body with a container neck is proposed, wherein a delivery head is fastened to the container neck, said delivery head having a delivery opening and liquid being able to be delivered through said delivery opening from the squeezable bottle body. Preferably, the dispenser is a droplet dispenser for the discharge of individual droplets, in particular for ophthalmic use. The delivery head of such a droplet dispenser preferably has droplet formation means, in particular in the form of a planar or conical droplet formation surface on which the delivered liquid collects until it is released as droplets from the droplet formation surface. Such a droplet dispenser preferably has an outlet valve arranged upstream of the delivery opening, in particular when the liquid contained therein is free of preservatives.

In order to prevent the inadvertent compression of the squeezable bottle body, in particular if this is attempted by young children, according to the first aspect of the invention the liquid dispenser has a first cover body which in turn has at least one locking wall and defines at least one actuating recess. This first cover body is provided so as to be captive, and movable between a locked position and an open position on the liquid dispenser, and as a result is displaceable relative to the squeezable bottle body.

In the locked position, the first cover body covers a partial region of the squeezable bottle body by means of the locking wall such that a compression of the squeezable bottle body is prevented or at least impeded. In the open position, the first cover body opens the aforementioned partial region of the squeezable bottle body by means of the actuating recess, such that a compression of the squeezable bottle body is possible.

In order to use the liquid dispenser, the user displaces the cover body into the open position. After completing the delivery process, the user displaces the cover body back into the locked position in which an inadvertent delivery of liquid is prevented.

The squeezable bottle body may have the capacity to be pushed-in non-uniformly over the periphery due to its shaping or wall design. In such a case, the at least one partial region which may be covered by the locking wall is a surface portion which is able to be pushed-in in a particularly simple manner. If the cover body is in its locked position, the compression of the squeezable bottle body is impeded thereby, such that only a partial region of the squeezable bottle body which is tougher or not able to be pushed in is accessible.

Preferably, a second cover body is also provided. This second cover body also has at least one locking wall and defines at least one actuating recess. The first cover body is displaceable relative to this second cover body, such that in the open position the actuating recesses overlap or are even congruent, such that it is possible to apply force onto the squeezable bottle body through both actuating recesses. If the first cover body is in the locked position, however, the actuating recesses are offset relative to one another such that an actuation of the squeezable bottle body is prevented or at least impeded.

In the locked position, the locking portions of both cover bodies may surround an outer wall of the squeezable bottle body, in particular by means of their locking portions, over the entire periphery or virtually entirely (>80%).

The cover bodies are preferably configured as shell bodies surrounding the squeezable bottle body.

The first cover body is preferably configured to be rotatable relative to the squeezable bottle body, in particular about a main axis in which the delivery opening is also located and/or about a central axis of the squeezable bottle body. The second cover body is preferably attached to the squeezable bottle body, fixedly in terms of rotation relative thereto, in particular preferably by means of a clamped connection. However, a design is also encompassed by the invention in which both cover bodies are movable and in particular are rotatable relative to the squeezable bottle body and relative to one another.

The first and/or the second cover body preferably has a substantially rotationally symmetrical sleeve portion in which the at least one actuating recess is provided in the form of a through-hole. The sleeve portions preferably have a length which permits them to extend from the upper end of the squeezable bottle body as far as the bottom thereof. The at least one through-hole is configured as a recess which is surrounded on all sides by the respective sleeve portion.

One possible design provides that exactly one throughhole is provided on the first or on the second cover body. For the compression, the user exerts a force with at least one finger through the through-hole directly onto the squeezable bottle body. No further through-hole is provided opposite the one through-hole, so that in this case a force is exerted by the user directly on the sleeve portion and only indirectly on the squeezable bottle body. In the case of such a design with only one through-hole on the first and optionally on the second cover body, in the peripheral direction this throughhole preferably spans an angular range of between 120° to 240°, in particular preferably an angular range of between 150° and 210°.

A design is preferred in which two through-holes opposing one another are provided on the first or on the second cover body. For compressing the squeezable bottle body, the user exerts a force onto the squeezable bottle body with in each case at least one finger, in particular with the index finger and thumb, through the through-holes which oppose one another. In the case of such a design it is preferably provided that the two through-holes in each case span an angular range of between 60° and 170°, preferably in each case an angular range of between 90° and 160°.

If two cover bodies are used, they are preferably arranged in the manner of an inner shell and an outer shell surrounding the squeezable bottle reservoir, wherein a simple design provides that the first cover body is arranged externally and the second cover body is arranged internally and is preferably provided fixedly in terms of rotation on the squeezable bottle body. As a result, in the locked state the locking wall of the second cover body is arranged between the squeezable bottle body and the locking wall of the first cover body.

However, a construction is also possible in which the second cover body, which is preferably provided fixedly relative to the squeezable bottle body, forms the outer shell and the first movable and preferably rotatable cover body forms the inner shell.

The squeezable bottle body, the first cover body and optionally the second cover body are preferably produced in each case as one-piece components from plastics. For the assembly, the first and optionally the second cover body are preferably pushed from above or preferably from below onto the squeezable bottle body. Preferably, the first and/or the second cover body has latching means in order to be latched axially on the other cover body or on the squeezable bottle reservoir or on the delivery head.

The cover bodies may have at least one deflectable securing portion which is resiliently widened when the cover body is pushed on and in the end position at least partially relaxes again. In particular, such a resiliently deflectable securing portion may be provided on the second cover body, in order to prevent the squeezable bottle body from being pulled out of the second cover body after the second cover body has been pushed onto the squeezable bottle body.

In particular, the first cover body preferably has a support surface, during the course of assembly the resilient deflectability of the securing portion of the second cover body being restricted thereby after the first cover body has been pushed onto the second cover body. The first cover body accordingly secures the second cover body on the squeezable bottle body.

In particular, a plurality of radially deflectable securing portions may also be provided. Preferably, at least one of the cover bodies has two such securing portions, wherein during assembly the squeezable bottle body pushes these securing portions away from one another, in order to pass through. In the case of a design with a plurality of securing portions, it is preferably provided that a common and preferably peripheral support surface is provided, the radial deflectability thereof being restricted after the assembly is completed.

It is advantageous if the first cover body is lockable in at least one of the positions, i.e. the locked position and the open position. A design is also conceivable in which, due to a high rotational resistance, the respective position is retained only by a frictional connection. Preferably, however, a switchable locking is provided, the first cover body being lockable in terms of rotation thereby on the squeezable bottle body, on the second cover body or on the delivery head. This locking is preferably implemented by positively-acting locking elements which, in particular, may counteract a rotational movement. If the locking elements are in engagement with one another, a movement of the first cover body is not possible. The locking elements are arranged such that such a locked state is possible in the locked position or in the open position or in both positions.

In order to bring the locking elements out of engagement, preferably one of the bodies, in particular the first cover body, is resiliently deformed. In particular, to this end it may be provided that one of the cover bodies has a resiliently deformable peripheral annular segment, external unlocking surfaces which oppose one another being provided thereon, and a locking element arranged in the peripheral direction between the unlocking surfaces being provided internally thereon. By the application of force on the unlocking surfaces oriented toward one another, the annular segment is compressed and the locking element deflected outwardly, wherein the engagement with an internal locking element, in particular on the second cover body, is released.

It may also be provided that an insulated, resiliently deflectable locking element which is displaceable, in particular pivotable, by a manual application of force, is provided on the cover body or on the second cover body. This displacement permits the deflectable locking element to be brought out of engagement with a corresponding locking element on the other cover body or on the squeezable bottle body.

Since it is preferred, in particular, that the cover bodies may be rotated relative to one another for achieving the locked state or the open state, it may be advantageous if a gripping surface is provided to this end on at least one of the cover bodies. A design in which the second cover body has an at least approximately peripheral gripping surface is, in particular, advantageous. This gripping surface is preferably provided with a structuring, in particular with a regular pattern of elevations or depressions. The gripping surface is preferably provided on the outside on the above-described deflectable securing portions.

A second aspect of the invention relates to a liquid dispenser with a delivery device and a cap. The liquid dispenser has a liquid reservoir, in particular formed by a squeezable bottle body, and a delivery head with a delivery opening. The cap covers the delivery opening and is able to be removed for the purpose of the discharge of liquid and is able to be replaced after use.

The cap has a cap body and a locking ring which is rotatably attached to the cap body. Locking profiles which face one another in the positioned state are provided on the delivery device, in particular on the delivery head, and on the locking ring. These locking profiles prevent a removal of the cap in at least one securing-rotational position of the locking ring by means of a positive connection. The locking profiles are configured such that a removal of the cap is only possible when the locking ring has been rotated relative to the delivery device into an opening-rotational position.

The locking ring is captively connected to the cap body. Preferably, the cap body and the locking ring have cooperating latching means, the cap body and the locking ring being latchable thereby, ensuring the rotational mobility, when the cap body is pushed from below into the locking ring during the course of assembly.

The locking ring and the cap body are preferably connected together so as to be secured against rotation in the delivery state, such that the state of rotatability has to be first produced, in particular, by a deformation or removal of a partial portion of the locking ring or the cap body. In particular, this rotationally securing partial portion may be irreversibly removed, as is intended, for example broken off.

At the same time it also represents a tamper-evident portion, the removal thereof signalling that the liquid dispenser has already been put into operation.

In one possible embodiment, it is possible to pull off the cap immediately after rotating the locking ring into the open position. In the open position, with such a design the locking ring does not provide any resistance to the cap being pulled off.

Preferably, however, it is provided that the locking profiles which face one another are configured such that a removal of the cap is not immediately possible in the opening-rotational position of the locking ring but only if the locking ring or a partial portion of the delivery device is also resiliently deformed.

For removing the cap, the user thus has to rotate and then deform, in particular compress, the locking ring in order to release the cap. For an adult this does not represent a particular difficulty since a rotation and compression of the locking ring and pulling off the cap may be carried out in one hand movement. However, it is difficult for a young child to understand which partial movements are required. Additionally, with a suitable design, the required deformation of the locking ring may be greater than the strength of a young child.

In particular, it may be provided that the locking ring has on opposing sides opening-actuating surfaces. If these opening-actuating surfaces are pushed radially toward one another in the opening-rotational position, the locking profile on the locking ring is displaced radially outwardly such that a removal of the cap is then possible, in particular simply by pulling off.

A design in which the delivery device and the locking ring have orientation markings, which are oriented so as to coincide when the locking ring is in its open position, is preferred. As a result, in the current position of the locking ring it is easily visible whether the cap is locked or removable.

In particular, the orientation marking is preferably arranged on the delivery device, such that it is concealed by the locking ring when this locking ring is not in the open position. In this case, a recess may also be provided in the locking ring, the orientation marking of the delivery device being visible through said recess when the locking ring is in the open position.

As already shown, according to both aspects of the invention the liquid dispenser is preferably configured as a droplet dispenser for the discharge of individual droplets, in particular as a droplet dispenser for ophthalmic use. In the embodiment as a droplet dispenser, the liquid dispenser preferably has droplet formation means, in particular in the form of a planar or conical droplet formation surface.

The liquid reservoir of a liquid dispenser according to the invention which is formed, in particular, by the described squeezable bottle body preferably has a receiving volume of between 2 ml and 100 ml, in particular preferably of between 4 ml and 15 ml.

BRIEF DESCRIPTION OF THE DRAWINGS

Further advantages and aspects of the invention emerge from the claims and from the following description of preferred exemplary embodiments of the invention, which are described hereinafter with reference to the figures.

FIGS. 7A and 7B show the cap of the dispenser according to the second exemplary embodiment.

FIG. 8 shows the delivery head of the dispenser according to the second exemplary embodiment with the cap removed.

DETAILED DESCRIPTION OF THE EXEMPLARY EMBODIMENTS

Figure 1:
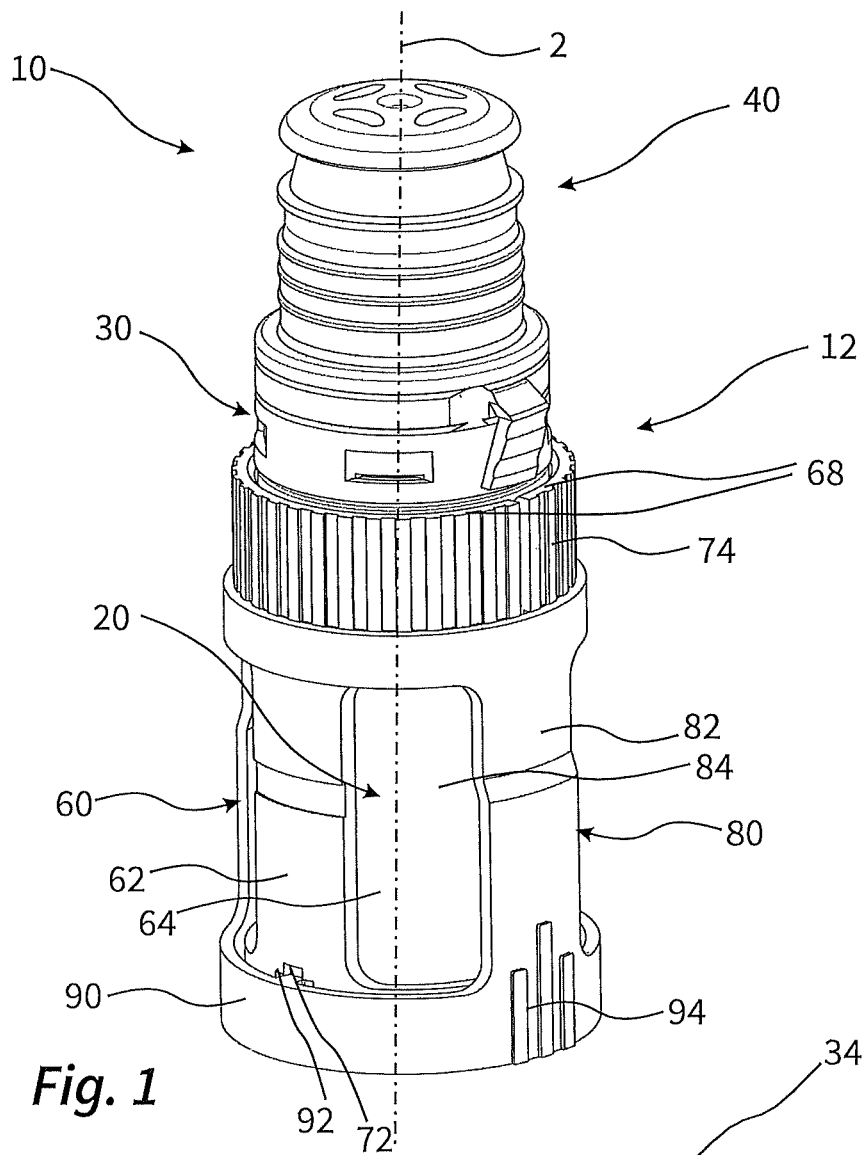
FIG. 1 shows a first exemplary embodiment of a dispenser according to the invention.

FIG. 1 shows a liquid dispenser 10 which serves for the delivery of eye drops but which may also be configured for further pharmaceutical uses, in particular for the discharge of droplets.

The liquid dispenser comprises a delivery device 12 with a liquid reservoir in the form of a squeezable bottle body 20 and a delivery head 30, as well as a cap 40. The cap 40 covers a delivery opening 32 and a droplet formation surface 34 on the delivery head 30. After being removed for the first time, the cap 40 may be repeatedly removed and repositioned for the purpose of using the liquid dispenser.

In a manner not shown in more detail, the delivery head 30 additionally comprises an outlet valve which may be opened by the application of the pressure of the liquid in the squeezable bottle body 20 so that liquid may flow to the delivery opening and collects in the upside-down position of the delivery device 12 on the droplet formation surface until the droplet is released.

In order to ensure a simple handling and meterability, the squeezable bottle body 20 may be compressed even with a small application of force. This is associated, however, with the risk that the squeezable bottle body 20 is inadvertently compressed, for example in a pocket or in luggage or by a young child.

In order to prevent this, a securing mechanism which is formed primarily by a first cover body 80 and a second cover body 60 is provided. The two cover bodies 60, 80 surround the squeezable bottle body 20 in the assembled state of FIG. 1. Both cover bodies 60, 80 are formed as sleeve portions 66, 86, each of which has a shape which is substantially sleeve-shaped or approximately cylindrical, wherein the sleeve portions 66, 86 each include a locking wall 62, 82. Each locking wall 62, 82 is provided with through-holes 64, 84 opposing one another.

At least one of the cover bodies 60, 80 is configured to be rotatable relative to the squeezable bottle body 20 and relative to the other cover body 60, 80 about the central axis 2, so that the respective through-holes 64, 84 are aligned with one another or offset to one another depending on the relative rotational position of the cover bodies 60, 80 to one another.

Figure 2A:
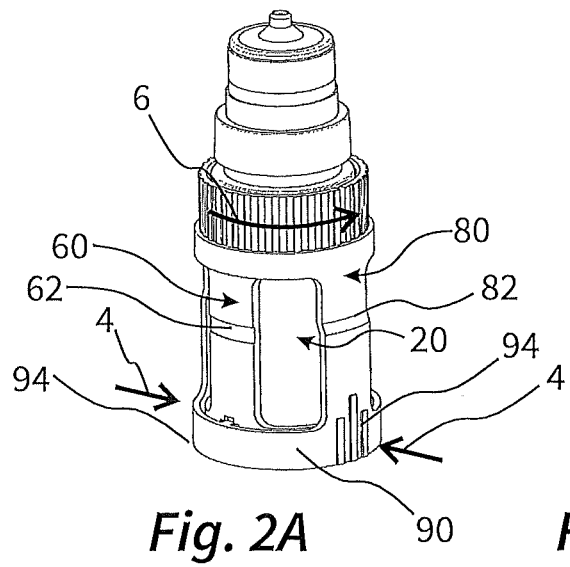
FIGS. 2A and 2B show the process of transferring the dispenser from its locked state into its open state.

FIG. 2A shows the state in which the through-holes 64, 84 are offset relative to one another and, as a result, a secured state of the delivery device 12 is achieved. Due to the size of the through-holes 64, 84 in the design shown, whilst the locking walls 82, 62 do not protect the squeezable bottle body 20 entirely, the remaining openings are not large enough for the squeezable bottle body 20 to be able to be inadvertently pushed-in to a significant degree and as a result liquid to be able to be discharged.

Figure 2B:
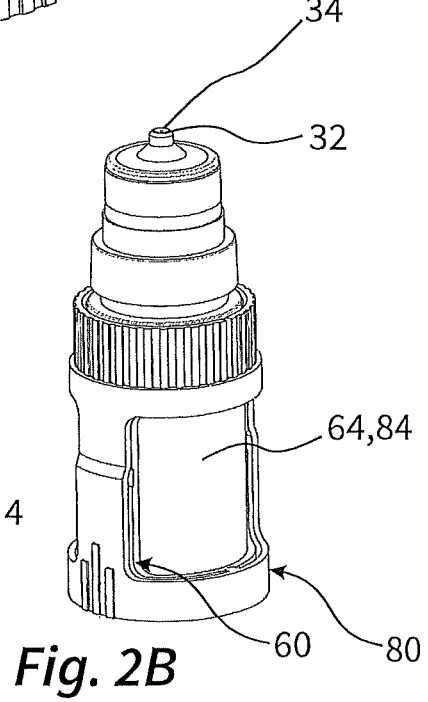

Proceeding from the secured state of FIG. 2A, in order to achieve a use state of FIG. 2B, the cover bodies 60, 80 have to be rotated relative to one another. However, this is not possible solely by a simple application of torque since a switchable locking 50, which in the locked state positively prevents a rotational movement, is provided. To this end, this locking comprises inwardly protruding locking elements 92 on the first cover body 80 which in the locked state are in engagement with locking elements 72 formed as recesses in the wall of the second cover body 60.

In order to release this locking, an annular segment 90 at which the first cover body 80 terminates at the bottom, has to be deformed. To this end, this annular segment 90 has unlocking surfaces 94 which oppose one another. If a force is exerted thereon in the direction of the arrows 4, the annular segment 90 is deformed and the locking elements 92 are displaced radially outwardly so that the engagement with the locking elements 72 of the second cover body 60 is released. In this unlocked state, the rotational movement in the direction of the arrow 6 is now possible so that the use state of FIG. 2B is achieved.

Figure 3A:
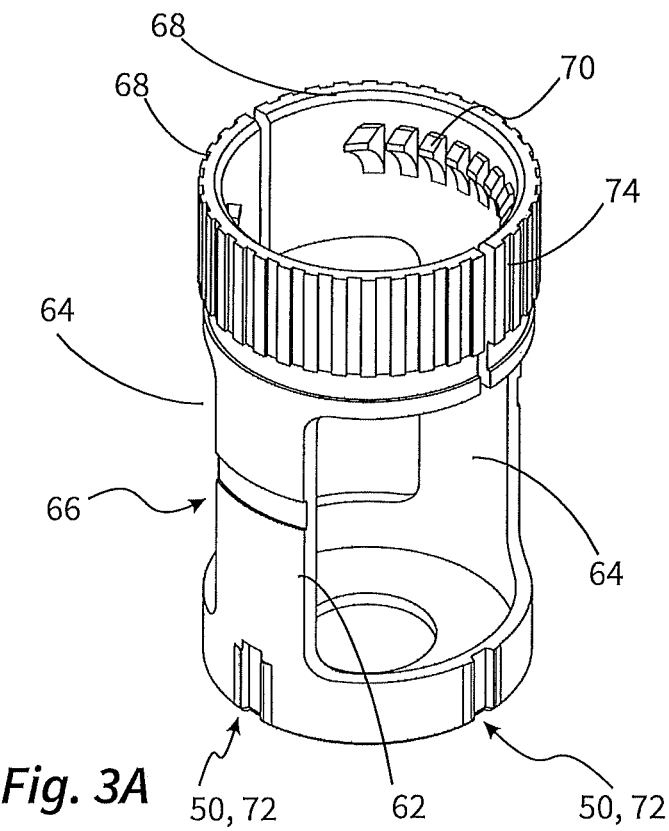
FIGS. 3A and 3B show two cover bodies of the dispenser.
Figure 3B:
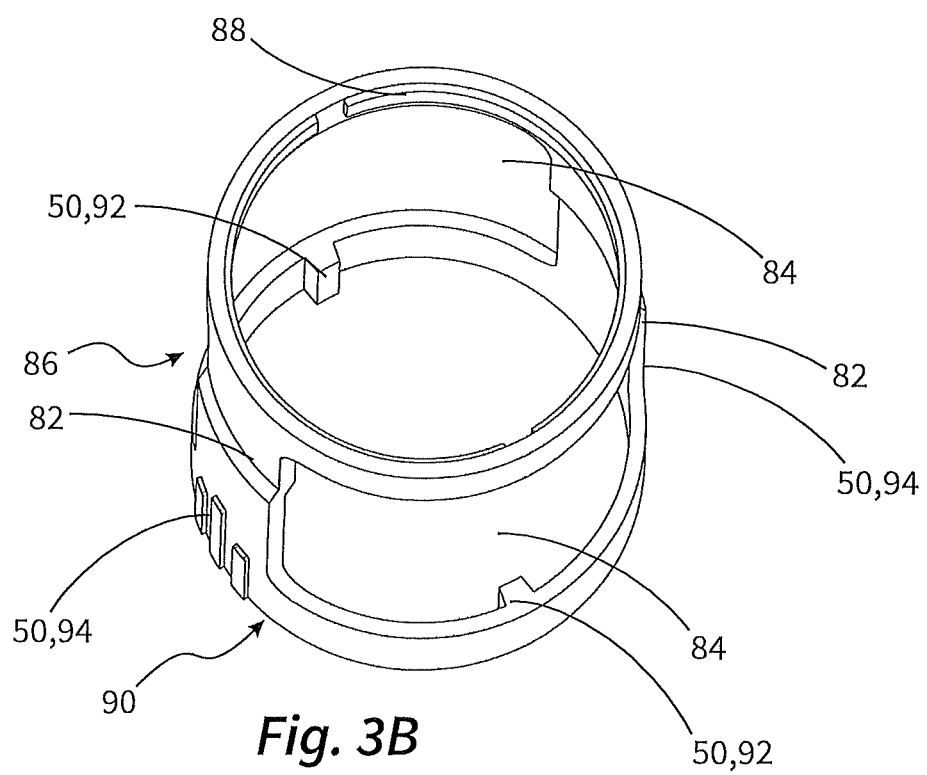
Figure 3C:
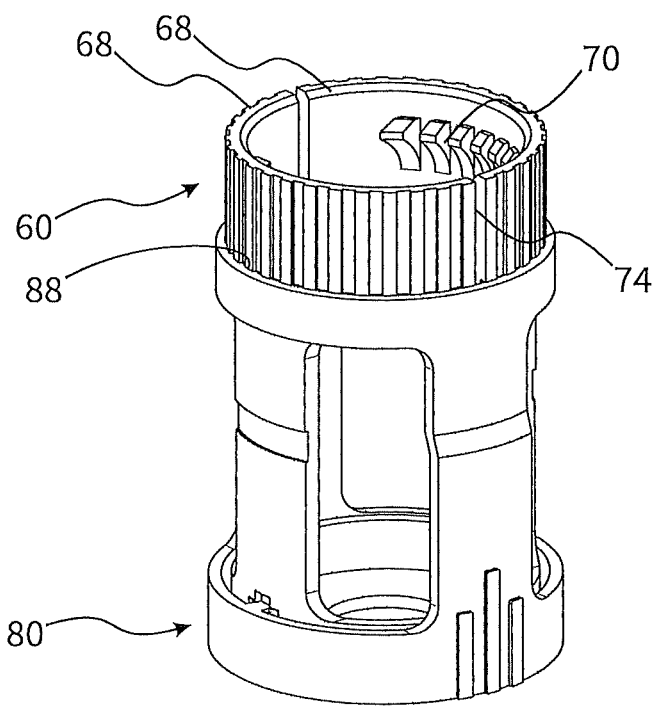
FIG. 3C shows the cover body in the assembled state.

FIGS. 3A to 3C show the cover bodies 60, 80 in each case in a separate and in an assembled view.

FIG. 3A shows the second cover body 60, which in the present exemplary embodiment forms the inner cover body. The body of the second cover body 60 is divided into two in the region of the upper end. Two approximately semicircular securing portions 68 are provided, the outer face thereof forming a substantially peripheral gripping surface 74. The securing portions have a retaining contour 70 on the inner face. By dividing the upper end of the second cover body 60 into two, the second cover body 60 may be widened when it is pushed from below onto the squeezable bottle body 20. Moreover, as shown in FIG. 3A, a total of four depressions, in each case offset by 90° are provided, the flanks thereof in each case forming the locking elements 72 for cooperating with the locking elements 92 of the first cover body 80. As a result, a rotational fixing of the cover bodies 60, 80 is possible both in the secured state and in the use state.

In the first cover body 80 shown in FIG. 3B, an upper annular portion forms a support surface 88 with its inner surface. The internal diameter thereof is adapted to the external diameter of the second cover body below the gripping surface 74.

In the assembled state of the cover bodies 60, 80, this leads to the support surface 88 preventing the two semicircular securing portions 68 from being able to be deflected outwardly. As a result, after being attached to the squeezable bottle body 20 the second cover body 60 is in turn prevented from being able to be released therefrom.

Figures 4A, 4B, 4C:
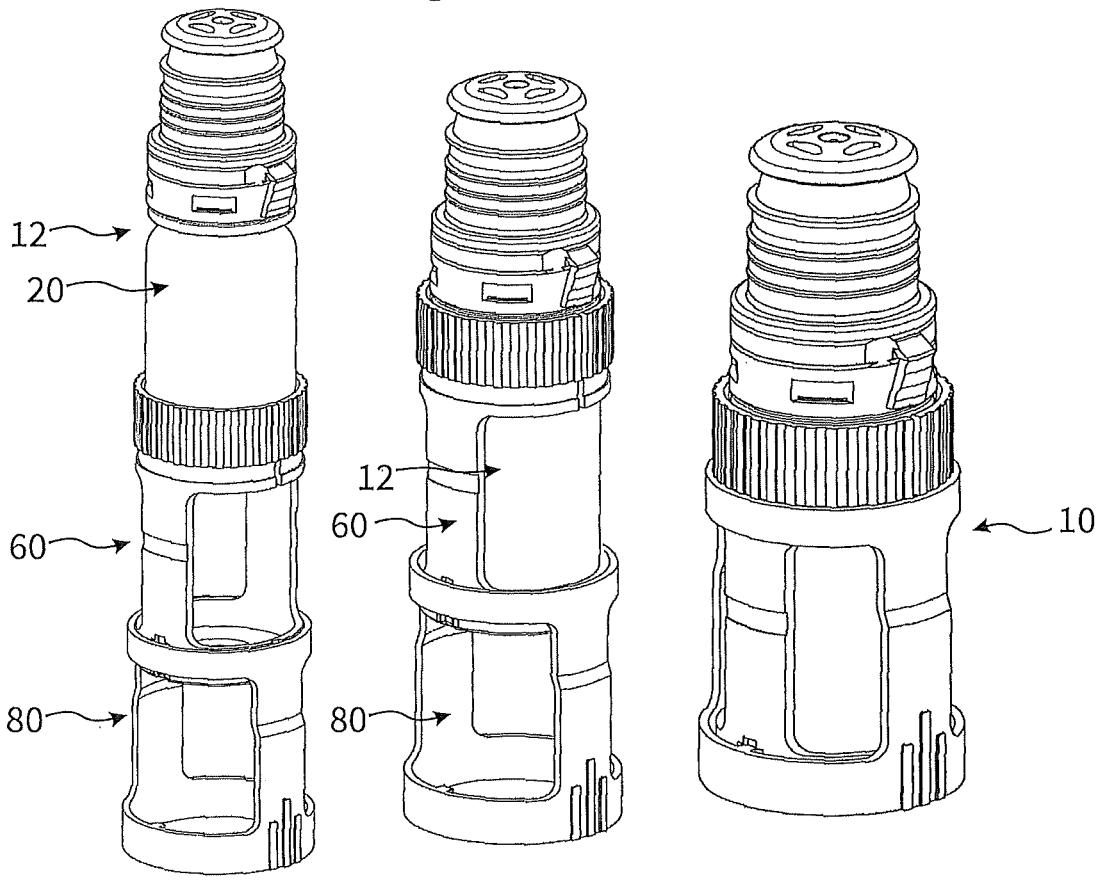
FIGS. 4A to 4C illustrate the assembly of the dispenser.

FIGS. 4A to 4C illustrate the assembly. As FIGS. 4A and 4B show, the delivery device 12 comprising the squeezable bottle body 20 is initially pushed into the second cover body 60. In this case, the aforementioned securing portions 68 are deflected. As soon as the squeezable bottle body 20 is fully received in the second cover body in the manner shown in FIG. 4B, the securing portions 68 are returned again into their initial position and retain the squeezable bottle body 20 by means of the retaining contour 70.

In the next step, the first cover body 80 is now pushed-on in the manner visible in FIGS. 4B and 4C. The support surface 88 thereof latches below the gripping surface 74 of the second cover body 60 so that a widening of the second cover body 60 is no longer possible. At the same time, the first cover body 80 is also secured thereby against being axially pulled off.

FIGS. 4A to 4C show a design in which the two cover bodies 60, 80 are already coupled together in the initial state of assembly in FIG. 4A and form a preassembled unit. Whilst this is preferred, it is also possible to connect together the cover bodies 60, 80 first during assembly.

FIGS. 5A to FIG. 8 illustrate the second aspect of the invention with reference to a second exemplary embodiment of a liquid dispenser 110. A delivery device 112 with a delivery head 130 and a squeezable bottle body 120 are also used here. The delivery device 112 is substantially identical to that of FIGS. 1 to 4, except for the cover bodies 60, 80, and may also be provided with the described cover bodies 60, 80. Coinciding with the exemplary embodiment of FIGS. 1 to 4, the delivery head 130 has a delivery opening 132 which is surrounded by droplet formation means 134. The particularity of the design of FIGS. 5 to 8 is in the cap 140. This cap has a one-piece cap body 142. A locking ring 144 is pushed onto a lower edge of this cap body 142. The cap body 142 and the locking ring 144 are permanently connected together by means of a peripheral collar 142A on the cap body 142 and latches 144A on the locking ring 144. However, the connection is sufficiently smooth-running so that in the use state the locking ring 144 is freely rotatable relative to the cap body 142, in particular when the cap body 142 is pushed in a clamped manner onto the delivery device 112 and thus in turn is not, or is barely, rotatable relative to the delivery device 112.

Figure 5A:
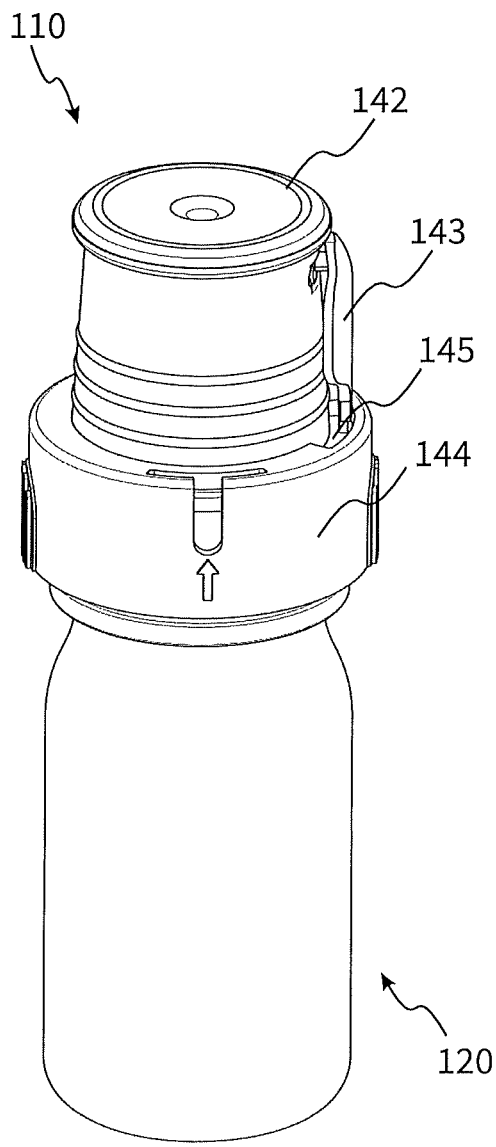
FIGS. 5A and 5B and 6 show a second exemplary embodiment of a dispenser according to the invention.

In the delivery state of FIG. 5A, the aforementioned rotatability is not yet provided since a plastics tongue 143, which also serves as a tamper-evident portion, protrudes into a recess 145 of the locking ring 144 and thereby forms a protection against rotation. For illustration, the plastics tongue 143 is also shown by dashed lines in FIG. 7B.

Figure 5B:
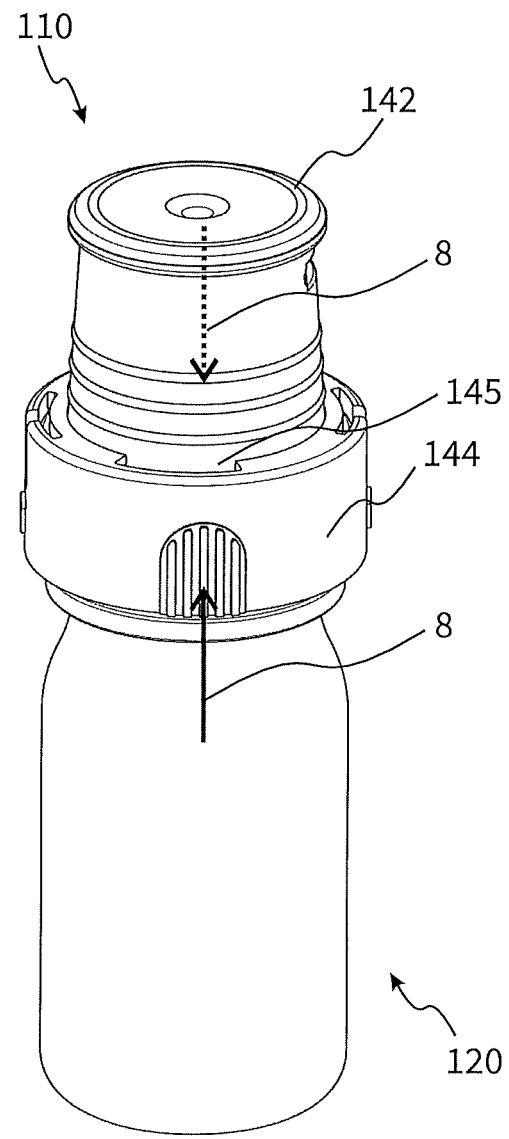

The rotational movement is possible only when this plastics tongue 143 has been removed from the cap body 142. This use state with the already rotated locking ring 144 is shown in FIG. 5B.

Figure 6:
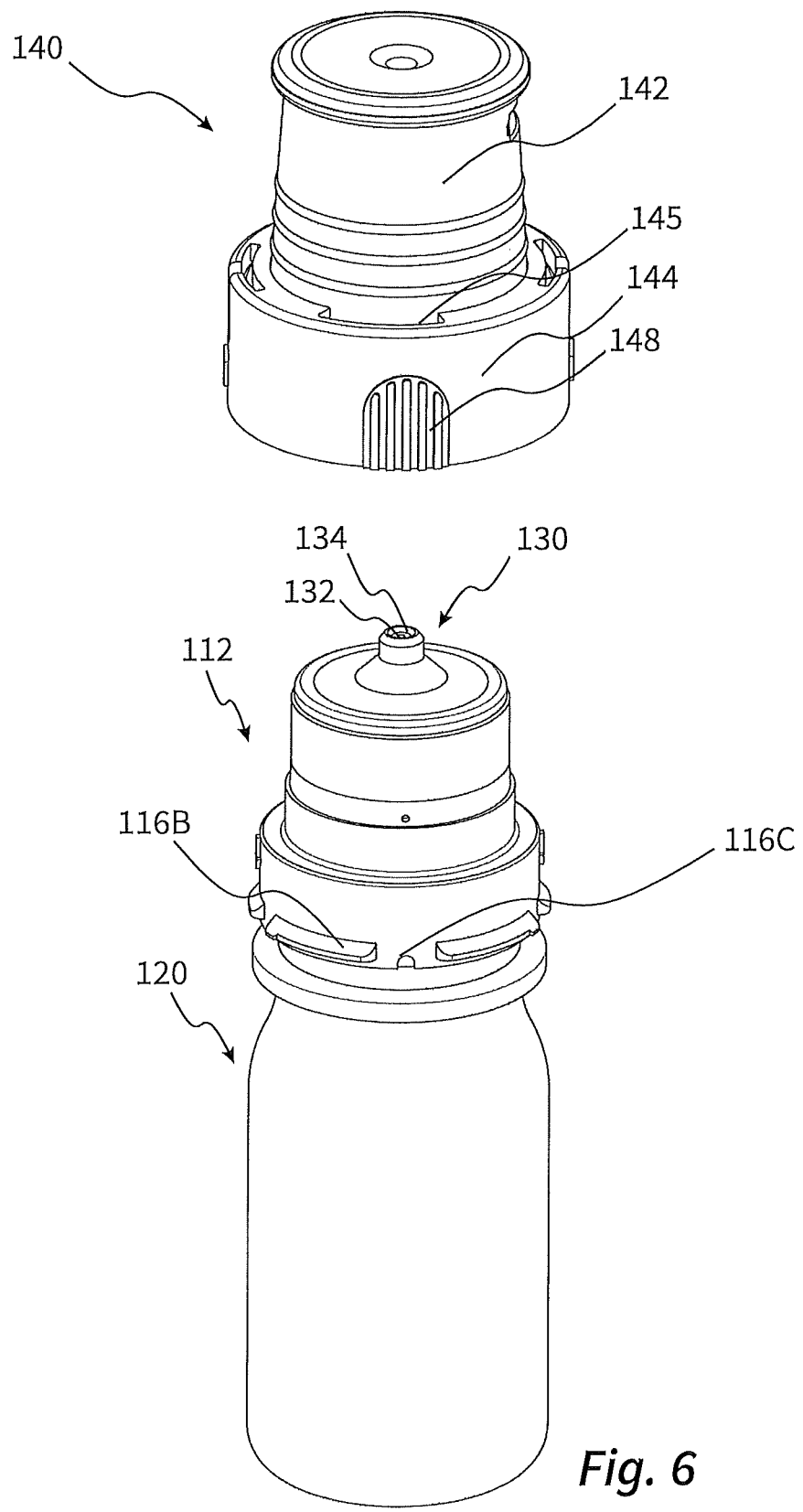

FIG. 6 shows the dispenser ready for use with the cap 140 removed.

The cap 140 may be fastened securely to the delivery device 112 by means of the locking ring 144. As is visible with reference to FIGS. 7A and 7B, locking profiles 146 in the form of inwardly facing projections with insertion bevels on the lower face are provided on the inner face of the locking ring 144. Correspondingly thereto, locking profiles 116A, 116B are also provided on the delivery head 130. This is shown in FIG. 8.

If the cap 140 is positioned on the delivery device 112, the locking profiles 146 engage below the locking profiles 116A, 116B and prevent the cap 140 from being easily pulled off.

In order to pull off the cap 140, the locking profiles 146 have to be displaced radially outwardly. This is possible due to the provision of opening-actuating surfaces 148 offset by 90° to the locking profiles 146, which opening-actuating surfaces 148 are pushed radially toward one another in the direction of the arrows 8 as illustrated in FIG. 5B.

However, a deflection of the locking profiles 146 required for releasing the coupling of the locking profiles 116A, 116B, 146 is not possible in every rotational position of the locking ring 144. A sufficient deformation is possible only in the rotational position of FIG. 5B in which the opening-actuating surfaces 148 are arranged in the region of a recess 116C between the locking profiles 116B, and the locking profiles 146 are arranged in the region of the locking profiles 116A.

In order to be able to identify the suitable orientation, orientation markings 119, 149 are provided. The orientation markings 119 on the delivery device 112 consist of a symbol, in the present case an arrow symbol, on an outer surface of the delivery head 130. The orientation marking 149 of the cap 140 comprises a through-hole, the orientation marking 119 on the delivery head 130 being identifiable through said through-hole from the outside in the case of a suitable orientation.

Whilst when removing the cap 140 the locking ring 144 has to be brought initially into the suitable orientation, depending on the design of the cap this may be dispensed with during the positioning of the cap. This is achieved by suitable insertion bevels on at least one of the locking profiles 116A, 116B, 146.

The invention claimed is:

1. A liquid dispenser for discharge of pharmaceutical liquids, the liquid dispenser comprising:
 a squeezable bottle body having a container neck;
 a delivery head fastened to the squeezable bottle body, the delivery head having a delivery opening through which delivery opening liquid is delivered from the squeezable bottle body; and
 a first cover body having at least one locking wall and defining at least one actuating recess,
 the first cover body being provided so as to be captive and movable on the liquid dispenser, wherein
 in a locked position the first cover body covers a partial region of the squeezable bottle body via the at least one locking wall, such that a compression of the squeezable bottle body is prevented or at least impeded, and in an open position the first cover body opens the partial region of the squeezable bottle body via the at least one actuating recess such that a compression of the squeezable bottle body is possible.

2. The liquid dispenser according to claim 1, further including
 a second cover body,
 the second cover body having at least one locking wall and defining at least one actuating recess, and
 the first cover body is displaceable relative to the second cover body such that in the open position the actuating recesses overlap such that it is possible to apply force on the squeezable bottle body through both actuating recesses, and such that in the locked position the actuating recesses are offset relative to one another such that an actuation of the squeezable bottle body is prevented or at least impeded.

3. The liquid dispenser according to claim 2, wherein
 the first cover body is rotatable relative to the squeezable bottle body and/or relative to the second cover body, and a rotational axis of the first cover body coincides with a central axis of the squeezable bottle body.

4. The liquid dispenser according to claim 2, wherein
 the first and/or the second cover body has a substantially rotationally symmetrical sleeve portion, the at least one actuating recess of the first and/or the second cover body being in the form of a through-hole disposed in the sleeve portion.

5. The liquid dispenser according to claim 2, wherein
 the first and second cover bodies are arranged relative to one another such that in the locked position the at least one locking wall of the second cover body is arranged between the squeezable bottle body and the at least one locking wall of the first cover body.

6. The liquid dispenser according to claim 2, wherein
 the second cover body has at least one resiliently deflectable securing portion preventing the squeezable bottle body from being pulled out of the second cover body, and
 the first cover body has a support surface restricting a resilient deflectability of the securing portion of the second cover body.

7. The liquid dispenser according to claim 2, further including
 a switchable locking arrangement, the first cover body being lockable in terms of rotation by the switchable locking arrangement in the locked position such that the first cover body is secured against rotation on the second cover body or the squeezable bottle body.

8. The liquid dispenser according to claim 1, wherein
 the first cover body has a resiliently deformable peripheral annular segment having opposed external unlocking surfaces provided thereon, and the peripheral annular segment has at least one locking element provided internally thereon peripherally between the unlocking surfaces.

9. The liquid dispenser according to claim 2, further including
 a resiliently deflectable locking element provided on the first cover body or on the second cover body, said locking element being displaceable by a manual application of force such that the locking element is separated from a corresponding locking element on the other first or second cover body or on the squeezable bottle body.

10. A liquid dispenser for discharge of pharmaceutical liquids, the liquid dispenser comprising:
 a delivery device having a liquid reservoir and a delivery head with a delivery opening; and
 a replaceable cap, the cap in a positioned state covering the delivery opening and in a removed state opening the delivery opening for delivery of liquid,
 the cap having a cap body and a locking ring attached to the cap body for rotatable movement relative to the cap body;
 wherein the delivery device and the locking ring include respective locking profiles facing one another in the positioned state, said locking profiles preventing a removal of the cap in at least one securing-rotational position of the locking ring relative to the delivery device by a positive connection, and
 the locking profiles are configured such that a removal of the cap is only possible when the locking ring has been rotated relative to the delivery device into an opening-rotational position.

11. The liquid dispenser according to claim 10, wherein
 the locking profiles are configured such that a removal of the cap in the opening-rotational position is only possible if the locking ring or a partial portion of the delivery device is resiliently deformed.

12. The liquid dispenser according to claim 10, wherein
 the locking ring has on opposing sides opening-actuating surfaces, the opening-actuating surfaces, with a simultaneous application of force deflecting the opening-actuating surfaces radially toward one another in the opening-rotational position, radially outwardly displacing the locking profiles such that a removal of the cap is possible.

13. The liquid dispenser according to claim 10, wherein
 the cap body and the locking ring have cooperating latching structures configured to ensure rotational mobility of the locking ring relative to the cap body.

14. The liquid dispenser according to claim 10, wherein the delivery device and the locking ring have orientation markings oriented so as to positionally coincide with one another when the locking ring is in the opening-rotational position.

15. The liquid dispenser according to claim 1, wherein the liquid dispenser is configured as a dropper for discharge of individual droplets.

16. The liquid dispenser according to claim 2, wherein the second cover body has an at least approximately peripheral gripping surface formed with a regular pattern of elevations or depressions.

17. The liquid dispenser according to claim 3, wherein the second cover body is fixed in terms of rotation relative to the squeezable bottle body by a clamped connection between the second cover body and the squeezable bottle body, or the second cover body is rotatable relative to the squeezable bottle body and relative to the first cover body.

18. The liquid dispenser according to claim 4, wherein exactly one through-hole is provided on the first cover body or on the second cover body, the exactly one through-hole covering in a peripheral direction an angular range of between 120° to 240°, or two through-holes are provided on the first cover body or on the second cover body in opposed relation with one another, said two through-holes each covering an angular range of between 60° and 170°.

19. The liquid dispenser according to claim 6, wherein the support surface bears against the second cover body in a region of the resiliently deflectable securing portion on the second cover body, or the second cover body has a plurality of radially deflectable securing portions and the first cover body has a peripherally-extending support surface disposed to restrict radial deflectability of the plurality of securing portions.

20. The liquid dispenser according to claim 7, wherein the switchable locking arrangement includes positively-acting locking elements.

21. The liquid dispenser according to claim 10, wherein the liquid reservoir comprises a squeezable bottle body.

22. The liquid dispenser according to claim 13, wherein the locking ring and the cap body are connected together so as to be secured against rotation in a delivery state, the locking ring or the cap body including a frangible portion configured for removal in order to permit rotation of the locking ring.

23. The liquid dispenser according to claim 14, wherein the orientation marking on the delivery device is concealed by the locking ring when the locking ring is not in the opening-rotational position.

24. The liquid dispenser according to claim 23, wherein the orientation marking on the locking ring includes a recess disposed in the locking ring, the orientation marking of the delivery device being visible through said recess when the locking ring is in the opening-rotational position.

25. The liquid dispenser according to claim 15, wherein the liquid dispenser has a planar or conical droplet formation surface.

26. The liquid dispenser according to claim 1, further including a switchable locking arrangement, the first cover body being lockable in terms of rotation by the switchable locking arrangement in either or both of the locked position and the open position.

27. The liquid dispenser according to claim 10, wherein the locking ring is attached to the cap body for rotatable movement relative to the cap body about a central axis of the cap.

28. The liquid dispenser according to claim 10, wherein the locking ring is disposed in surrounding relation with the cap body and is fixedly attached thereto, and an entirety of the locking ring is rotatable relative to the cap body.

* * * * *